United States Patent [19]

Mulder

[11] Patent Number: Plant 6,767

[45] Date of Patent: May 2, 1989

[54] DAHLIA PLANT NAMED ELLY

[75] Inventor: Alle D. Mulder, Enkhuizen, Netherlands

[73] Assignee: Royal Sluis B.V., Enkhuizen, Netherlands

[21] Appl. No.: 131,197

[22] Filed: Dec. 10, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Dahlia plant named Elly, having white ray florets, double flower form, compact growth habit, dense foliage, a compact flower bouquet above the foliage, and an adaptability to pot plant or outdoor cultures.

1 Drawing Sheet

1

The present invention relates to a new and distinct cultivar of Dahlia plant known by the cultivar name Elly, and botanically known as *Dahlia cav.*

Elly was originated from a hybridization made by me in a controlled breeding program in 1983 in Enkhuizen, The Netherlands. The female or seed parent was a Dahlia cultivar which is no longer known. The male or pollen parent of Elly was a selected plant of the seed varieties commercially well known under the name Figaro. Elly was discovered and selected by applicant as one flowering plant within the progeny of the stated parentage in a controlled environment in Enkhuizen, The Netherlands.

The first act of asexual reproduction of Elly was accomplished when tuberous divisions were taken by me from the selection in a controlled environment in Enkhuizen, The Netherlands. Subsequent horticultural examination of selected units has demonstrated that the combination of characteristics as herein disclosed for Elly are firmly fixed and are retained through successive generations of asexual reproduction.

Elly has not been observed under all possible environmental conditions. The phenotype may vary significantly with variations in environment such as temperature, light intensity, and day length. The following observations, measurements and comparisons describe plants grown in Enkhuizen, The Netherlands under greenhouse and outdoor conditions which approximate those generally used in commercial practice.

The following traits have been repeatedly observed and are determined to be basic characteristics of Elly, which in combination distinguish this Dahlia as a new and distinct cultivar:

(1) White ray florets, with yellowing near center of yellow-orange disc florets.

(2) Double flower form.

(3) Dense foliage.

(4) Flowers are carried above the foliage in a compact bouquet.

(5) Compact growth habit.

(6) Adaptable to pot plant culture as well as natural outdoor growth.

Relevant cultivars for comparison purposes are varieties of Rigoletto, also a well known commercial dahlia series obtained from seed, and plants of Figaro. In comparison to Rigoletto, Elly is more compact, has a double flower form, and white ray florets. Elly is distinguished from Figaro by its more compact habit, its earlier flowering, and its white ray florets.

2

The accompanying color photographic drawing shows typical inflorescence and foliage characteristics of Elly, with colors being as nearly true as possible with illustrations of this type. The photograph is a perspective view of several potted plants of Elly.

In the following description color references are made to The Royal Horticultural Society Colour Chart. The color values were determined at Enkhuizen, The Netherlands, and the characteristics noted below are based on plants grown at the same location.

Classification:

*Botanical.*—*Dahlia cav.* cv Elly (Group IV, peony flowered, classification of International Dahlia Register, 1969).

*Commercial.*—Dahlia.

Parentage:

*Female parent.*—Unknown.

*Male parent.*—A plant of the Figaro series.

Plant:

*Form.*—Generally round.

*Size.*—Approximately 20 cm in height (from top of pot).

*Growth habit.*—Compact.

*Foliage.*—Size: Small (according to Group classification noted above); approximately 8 cm long and 4.5 cm wide. Quantity: Abundant, dense. Color: Dark Green. Shape: Narrow, generally ovate, edges serrated. Texture: Relatively dull.

Flowers:

*Form.*—Double.

*Shape.*—Overall inflorescence is generally flat, with petals having blunt or slightly rounded tips.

*Size.*—Individual ray florets approximately 3 cm long and 1.5 cm wide; overall inflorescence approximately 8 cm in diameter.

*Borne.*—On pedicals which are approximately 3.5 cm in length; top of the pedicel oriented at approximately 90° to the vertical axis of the plant; flowers carried compactly above the foliage.

*Stems.*—Color of both new stem and flowering stem is light green.

*Color.*—Fully open, upper surface 155b. Fully open, under surface 155b. Half open, upper surface 155b. Half open, under surface 155b.

*Reproductive organs.*—Normal.

I claim:

1. A new and distinct cultivar of Dahlia plant named Elly, as described and illustrated.

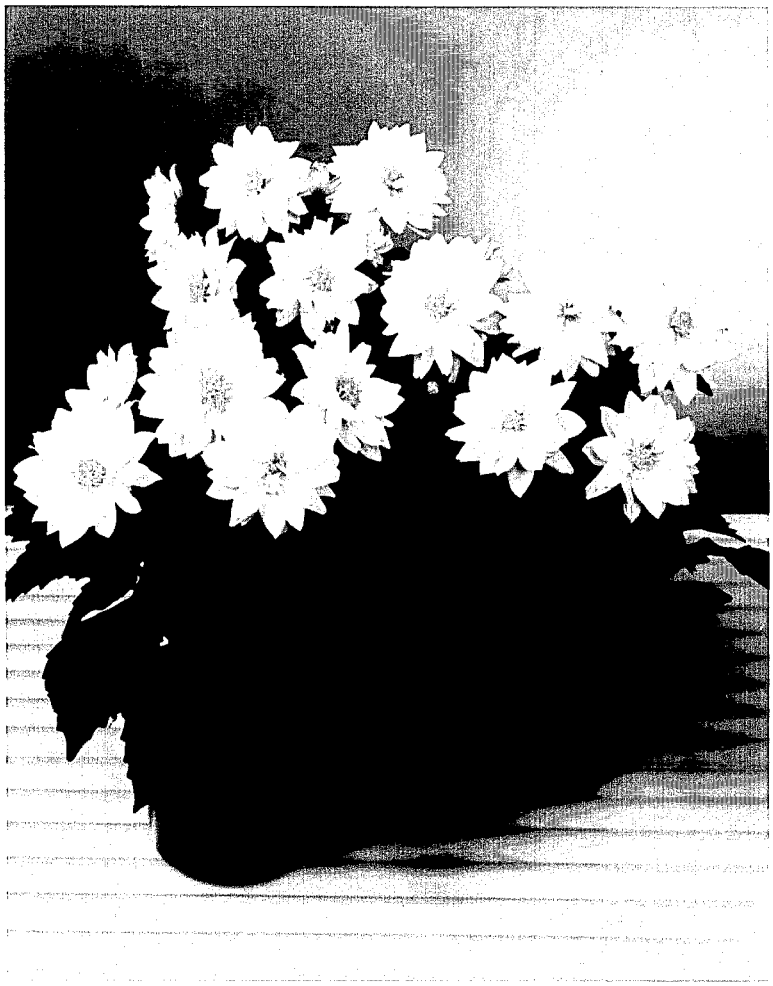

* * * * *